(12) United States Patent
Zanni

(10) Patent No.: US 9,638,634 B2
(45) Date of Patent: May 2, 2017

(54) MULTIDIMENSIONAL WHITE LIGHT SPECTROMETER

(71) Applicant: Wisconsin Alumni Research Foundation, Madison, WI (US)

(72) Inventor: Martin Thomas Zanni, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 112 days.

(21) Appl. No.: 14/804,965

(22) Filed: Jul. 21, 2015

(65) Prior Publication Data

US 2016/0018323 A1 Jan. 21, 2016

Related U.S. Application Data

(60) Provisional application No. 62/026,949, filed on Jul. 21, 2014.

(51) Int. Cl.
*G01J 3/46* (2006.01)
*G01N 21/63* (2006.01)

(52) U.S. Cl.
CPC ................................. *G01N 21/636* (2013.01)

(58) Field of Classification Search
CPC .... G01N 21/359; G01N 21/31; G01N 21/636; G01N 2021/653; G01J 3/433; G01J 3/2889; G02F 2001/3528
See application file for complete search history.

(56) References Cited

U.S. PATENT DOCUMENTS

| 4,512,660 A * | 4/1985 | Goldberg .................. G01J 3/44 356/301 |
| 5,479,256 A * | 12/1995 | Tamai .................. G01N 21/636 356/450 |
| 2008/0125977 A1* | 5/2008 | Anquetil ................ G01N 21/65 702/19 |
| 2009/0122319 A1 | 5/2009 | Ronnekleiv et al. |
| 2009/0161092 A1* | 6/2009 | Zanni ...................... G01J 3/433 356/51 |
| 2010/0110426 A1* | 5/2010 | Cicerone .................. G01J 3/02 356/301 |

OTHER PUBLICATIONS

Mikhailovsky; Basics of femtosecond laser spectroscopy; Full Document; Santa Barbara, CA.
Krebs et al.; Two-dimensional Fourier transform spectroscopy in the ultraviolet with sub-20 fs pump pulses and 250-720 nm supercontinuum probe; Journal; Downloaded from IOPscience; New Journal of Physics 15 (2013); pp. 1-17, Austria.
S. Bourquin et al.; High-speed femtosecond pump-probe spectroscopy with a smart pixel detector array; Optics letters 28, No. 17 (2003): 1588-1590; US.

* cited by examiner

*Primary Examiner* — Kara E Geisel
*Assistant Examiner* — Maurice Smith
(74) *Attorney, Agent, or Firm* — Boyle Fredrickson, S.C.

(57) ABSTRACT

A multidimensional spectrometer provides broadband white light pump and probe pulses to allow acquisition of multi-dimensional spectral information over a wide range commensurate with solar-related chemical processes.

20 Claims, 2 Drawing Sheets

MULTIDIMENSIONAL WHITE LIGHT SPECTROMETER

CROSS REFERENCE TO RELATED APPLICATION

This application claims the benefit of U.S. Provisional Application 62/026,949 filed Jul. 21, 2014, and hereby incorporated by reference.

STATEMENT REGARDING FEDERALLY SPONSORED RESEARCH OR DEVELOPMENT

This invention was made with government support under FA9550-12-1-0063 awarded by the USAF/AFOSR and 1121288 awarded by the National Science Foundation. The government has certain rights in the invention.

BACKGROUND OF THE INVENTION

The present invention relates to multi-dimensional optical spectrometers and in particular to a multi-dimensional optical spectrometer suitable for measurements over large frequency ranges.

Multi dimensional spectroscopy can reveal the interaction between coupled systems of atoms and/or molecules. For example, two-dimensional spectroscopy may provide an intuitively understandable two-dimensional spectrum in which the emission frequency of the system is plotted against the original excitation frequency. In a 2D spectrum, electromagnetic transitions of atoms or molecules matching the incident light give rise to signals that lie on the spectrum diagonal, but if there are interactions between transitions within or among molecules, then cross peaks will also appear in the spectrum. The diagonal and cross peaks can be used to deduce molecular structures or identify mixtures of compounds, etc. Multidimensional spectra of 3D or higher provide additional information.

To collect multidimensional spectrum, one needs to generate multiple light pulses to interrogate the sample. Typically a set of probe pulses are used to excite the sample which is then interrogated by a probe pulse. Some examples of two-dimensional spectroscopy are described in US patent application 2006/0063188 filed Sep. 15, 2005; US patent application 2009/0161092 filed Dec. 21, 2007; and US patent application 2012/0236305 filed Sep. 20, 2012, all hereby incorporated by reference.

Processes related to photosynthesis or solar energy, among others, could benefit from multidimensional spectrographic analysis; however, such analysis is challenging because of the large spectral range that must be analyzed, a range that can extend across the entire visible and near infrared wavelength region. Tuning the frequency of pump pulses over a large spectral bandwidth while preserving the necessary frequency and phase accuracy is difficult.

SUMMARY OF THE INVENTION

The present invention provides a multidimensional spectrograph that employs broadband "white light" for both pumping and probing pulses. By using broad spectrum pulses, center frequency tuning of the pulses is not required, eliminating the need for tuning mechanisms such as non-collinear optical parametric amplifiers or the like that be difficult to operate through a large range of frequencies.

Specifically, the present invention provides a multi-dimensional spectrometer having a white light source providing source light pulses having a substantially continuous bandwidth of at least 500 nanometers. A first optical system directs the source light pulses through a sample volume as a series of probe pulses to be received by a light detector while a second optical system receives the source light pulses to break the light pulses into at least first and second probe pulses having a controllable time separation between the first and second probe pulses. These first and second probe pulses are then directed through the sample volume before the probe pulse. An electronic computer system communicating with the light detector receives electrical data therefrom and controls the second optical system to change the time separation between the first and second probe pulses over multiple light pulses to generate a multi-dimensional spectrograph.

It is thus a feature of at least one embodiment of the invention to provide a multidimensional spectrometer that can accommodate measurements that require substantial spectral frequency range, for example, related to, but not necessarily limited to, chemical processes associated with photosynthesis or solar energy.

The light pulses may have a substantially constant center frequency.

It is thus a feature of at least one embodiment of the invention to provide a spectrometer that eliminates the need to tune the center frequency of narrowband pump pulses or probe pulses over a wide range, such tuning as may require expensive optical devices or be fundamentally impractical.

The light pulses may be generated by interaction between a laser and a spectrum-broadening crystal material to provide white light without modulation.

It is thus a feature of at least one embodiment of the invention to provide a simple method of generating a coherent white light source possible when frequency tuning is not required during the generation of the spectrograph.

The probe pulses may have a spectrum substantially identical to the source light pulses.

It is thus a feature of at least one embodiment of the invention to provide a simple generation of a probe pulse suitable for the entire measurement range.

The white light source may be either a laser passing through a beam splitter to be received by separate static spectral broadening elements or a laser received by a single static spectral broadening element and then passed to a beam splitter to create two source light pulses.

It is thus a feature of at least one embodiment of the invention to provide a flexible method of generating the necessary probe and pump pulses.

The second optical path may provide a bifringent crystal separating the light pulse into first and second differently polarized light pulses, the bifringent crystal followed by a polarization-selective wedge delaying one of the first and second differently polarized light pulses and not the other, followed by a polarizer realigning the polarization of the first and second differently polarized light sources after delay of the one of the first and second differently polarized light pulses wherein the position-selective wedge is controlled by the electronic computer.

It is thus a feature of at least one embodiment of the invention to provide a simple and robust method of controlling the separation between the pump pulses requiring only movement of the mechanical stage holding a wedge element.

At least one of the first and second optical paths may include a controllable pulse delay element for changing a relative delay of the probe pulse after the pump pulses.

It is thus a feature of at least one embodiment of the invention to permit adjustment of the data acquisition independently of control of the pump pulse separation.

These particular features and advantages may apply to only some embodiments falling within the claims and thus do not define the scope of the invention. The following description and figures illustrate a preferred embodiment of the invention. Such an embodiment does not necessarily represent the full scope of the invention, however. Furthermore, some embodiments may include only parts of a preferred embodiment. Therefore, reference must be made to the claims for interpreting the scope of the invention.

DETAILED DESCRIPTION OF THE PREFERRED EMBODIMENT

Figure 1:
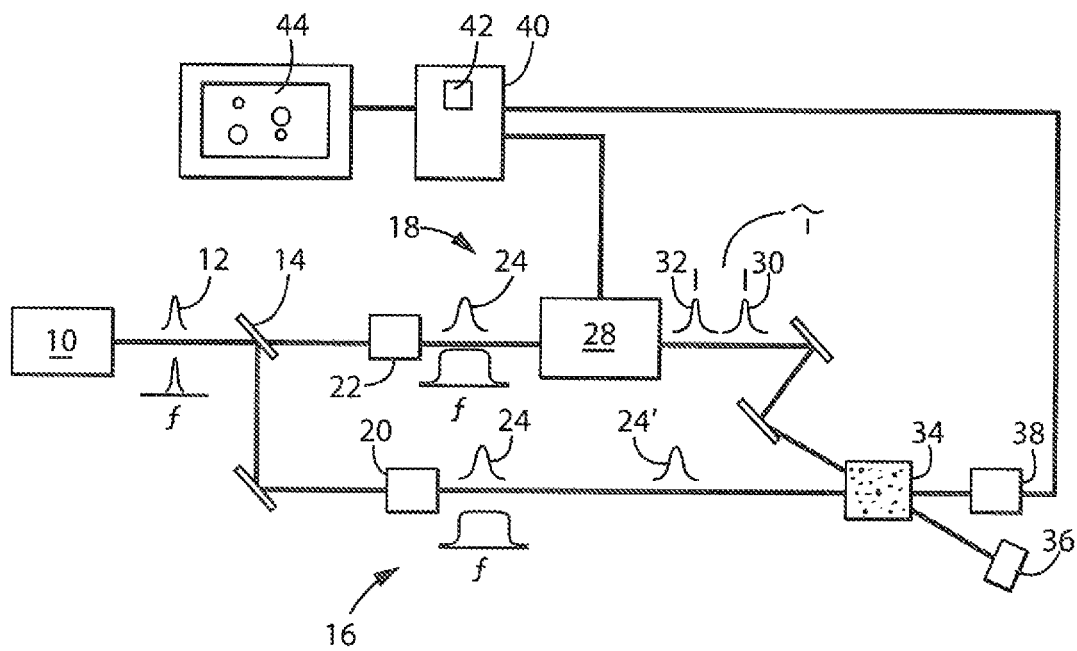
FIG. 1 is a simplified block diagram of the present invention showing the general principles using a white light pulse processed by a first optical system to produce a probe pulse and by a second optical system to produce pump pulses.

Referring now to FIG. 1, a laser 10 may provide a stream of pulses 12 directed to a beam splitter 14 directing part of the energy of each of the pulses 12 both to a first optical system 16 and second optical system 18 to develop probe and pump pulses respectively.

Pulses 12 output from the beam splitter 14 are received by a first and second spectrum-broadening crystal 20 and 22 each producing a supercontinuum white light pulse 24. A wavelength bandwidth of the white light pulses 24, for example, may range from wavelength between 400-1400 nanometers (and hence having a bandwidth of no less than 1000 nanometers). The invention contemplates a bandwidth of no less than 900 nanometers or no less than 700 nanometers. Generally the bandwidth will exceed 1½ octaves and will include the wavelength of 1000 nanometers.

In the first optical system 16, the white light pulse 24 may be received by a pulse splitter 28 which controllably splits the white light pulse 24 into first and second pump pulses 30 and 32 of substantially equal energy and frequency profile but separated in time by a time value $\tau$. The pump pulses 30 and 32 are directed through a sample volume 34 holding a sample to be analyzed (either by absorption or reflection). Pump pulses 30 and 32 leaving the sample volume 34 may be absorbed by an absorber 36.

In the second optical system 18, the white light pulse 24 is used as a probe pulse 24' and may pass through the sample volume 34 to be received by a detector 38, for example, a spectroscope, after stimulation of the material in the sample volume 34 by the pump pulses 30 and 32.

A signal from the detector 38 after receipt of the probe pulse 24' is received by an electronic computer 40 which may also control the pulse splitter 28 to change the value of $\tau$. Generally electronic computer 40 will execute a stored program 42 held in solid state memory or other non-transient memory structure to perform repeated "experiments" in which pump pulses 30 and 32 are used to excite material within the sample volume 34, which material is then analyzed by a probe pulse 24' (substantially identical in spectrum to white light pulse 24). Successive experiments may provide for different values of $\tau$ so as to generate information necessary to produce a two-dimensional spectrogram 44 of a type generally understood in the art. Individual experiments with the same value of $\tau$ may also be repeated and aggregated for the purpose of reducing measurement noise.

Figure 2:
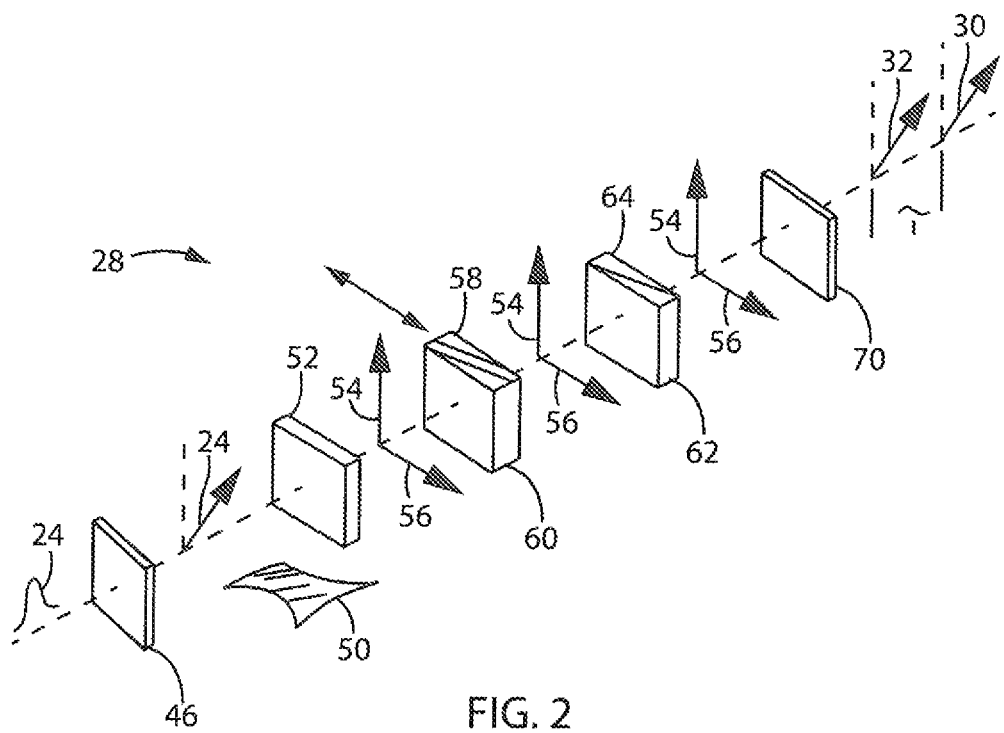
FIG. 2 is a detailed block diagram of a portion of the second optical system generating two pump pulses from a single white light pulse.

Referring now to FIG. 2, in one embodiment the pulse splitter 28 may provide a translating, wedge-based, identical pulse encoding system (TWINS), for example, as described in D. Brida, C. Manzoni, G. Cerullo, "Phase-locked pulses for two-dimensional spectroscopy by a birefringent delay line", Optics letters 37, 3027 (Aug. 1, 2012) hereby incorporated by reference.

In this system, a white light pulse 24 having a first polarization of 45 degrees with respect to a surface such as an optical table 50 (indicated in the figure by an arrow) is generated by a wave plate 46. The polarized white light pulse 24 is then received by an σ-BBO crystal 52 with an optical axis cut perpendicular to the surface of the table 50. The crystal 52 splits the white light pulse 24 into vertically and horizontally polarized pulses 54 and 56 with some fixed time delay between them.

Next a pair of α-BBO wedges 58 and 60 with optical axes cut parallel to the surface of the table 50 and perpendicular to the beam propagation axis are used to adjust the separation between pulses 54 and 56 by selectively delaying one pulse. This adjustment may be used to change value of $\tau$ in the pump pulses 30 and 32. Generally this adjustment is provided by physically moving one of the wedges (e.g. 58) by attachment of the wedge to the mechanical stage (not shown) controllable by the computer 40 (shown in FIG. 1) to change a thickness of the wedge intersecting the path of the pulses 54 and 56.

A second pair of wedges 62 and 64 downstream from wedges 58 and 60, with the optical axis cut parallel to both the surface of the table 50 and to the beam propagation, is used to fix the relative timing between the second pump pulse 32 and the probe pulse 24', as will be discussed below, as well as partially correcting the frequency dispersion of the two pump pulses 30 and 32 that would otherwise be generated by changing of the amount of material in the beam path with the first two wedges 58 and 60.

A polarizer 70 is used after the wedges 58, 60, 62 and 64 to realign the polarization of the pump pulses 30 and 32 to a common polarization and to set the final polarization of the pump pulses 30 and 32, for example, to be either parallel or perpendicular to the probe pulse 24'.

Figure 3:
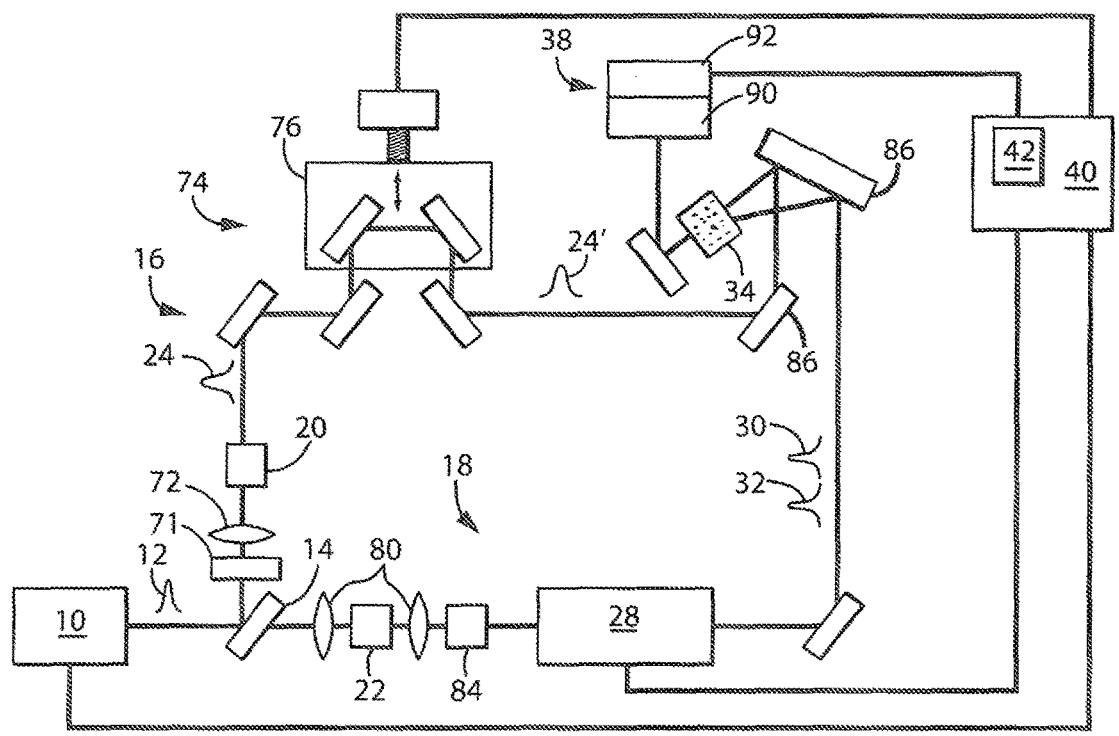
FIG. 3 is a more detailed diagram of the spectrometer of FIG. 1 using the second optical system of FIG. 2.
Figure 4:
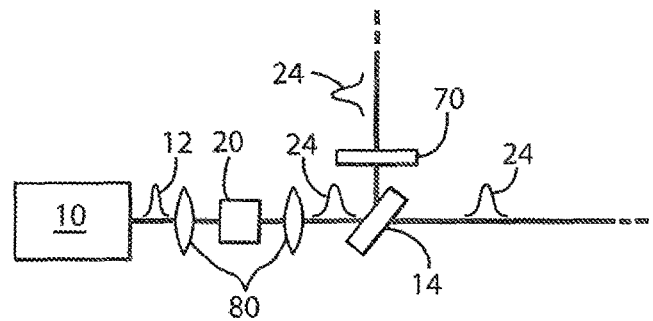
FIG. 4 is a fragmentary view of a portion of FIG. 3 showing an alternative method of generating white light pulses for the first and second optical systems.

Referring now to FIG. 3, the laser 10, for example, may in one example produce narrow spectrum pulses 12 having a center frequency of 800 nanometers and a duration of 150 femtoseconds with a one kilohertz repetition rate and a per pulse energy of 300 μJ. A laser suitable for this purpose is commercially available from Spectra Physics of California, United States under the trade name Spitfire.

After passing through the beam splitter 14, narrow spectrum pulses 12 may be received along the first optical path through a polarizing wave plate 71, collimating lens assembly 72 and spectrum-broadening crystal 20.

The white light pulse 24 is then received by a mirror array 74 providing an adjustable path length by means of a mechanically movable stage 76 controllable by the computer 40 as may be used to arbitrarily delay the white light pulse 24 with respect to the pump pulses 30 and 32 to produce the probe pulse 24'. The delay may be adjusted as necessary to capture the desired chemical phenomenon by the spectroscope.

After the beam splitter 14, narrow spectrum pulse 12 may also be received by a collimating optical assembly 80 on the second optical system 18 and by the second spectrum-broadening crystal 20 to produce white light pulse 24. Both spectral broadening crystals 20 and 22 may, for example, be four millimeter thick yttrium aluminum garnet (YAG) crystal.

A prism compressor 84 may then precompensate the white light pulse 24 against dispersion introduced by the pulse splitter 28. The white light pulse 24 is then is split into two pump pulses 30 and 32 following the pulse splitter 28.

The pump pulses 30 and 32 and probe pulse 24 are then received by a mirror array 86 to be focused through the sample volume 34 with light from the probe pulse 24' only being directed to the detector 38. The detector, for example, may be a 150 mm focal length spectrometer 90, for example, the Acton SP-2150 spectrograph commercially available from Princeton Instruments of New Jersey, United States, coupled with a light detector using an InGaAs photodiode array 92, for example, the OMA-V:512-1.7 also commercially available from Princeton Instruments.

Referring now to FIG. 3, it will be appreciated that an alternative method of generating the white light pulses 24 may direct the laser pulses 12 through collimating optical assembly 80 and a single spectrum-broadening crystal 20 before the beam splitter 14. The beam splitter may then split a single white light pulse 24 into two white light pulses 24.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References in the claims and specification to a first and second modulator should not be interpreted as limited to two devices in separate housings or to two devices having separate components but may be realized with any device, including a single device, operating to provide independent modulation of two different light beams according to independent modulation signals. Likewise, each of the first and second modulators may be composed of multiple modulators.

References to "a controller" and "a processor" can be understood to include one or more controllers or processors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

I claim:

1. A multi-dimensional spectrometer comprising:
   a sample volume holding a sample to be analyzed;
   a light detector proximate to the sample volume;
   at least one white light source providing source light pulses having a substantially continuous bandwidth of at least 500 nanometers;
   a first optical system directing the source light pulses through the sample volume as a series of probe pulses to be received by the light detector;
   a second optical system receiving the source light pulses to break the light pulses into at least first and second pump pulses having a controllable time separation between the first and second pump pulses and directing the at least first and second pump pulses through the sample volume; and
   an electronic computer system communicating with the light detector to receive electrical data therefrom and the second optical system to control the time separation between the at least first and second pump pulses over multiple light pulses to generate a multidimensional spectrograph.

2. The multidimensional spectrometer of claim 1, wherein the light pulses have a substantially constant center frequency.

3. The multidimensional spectrometer of claim 2 wherein the light pulses are generated by interaction between a laser and a spectrally-broadening crystal material to provide white light without modulation.

4. The multidimensional spectrometer of claim 1 wherein the light pulses have a bandwidth of at least 700 nanometers.

5. The multidimensional spectrometer of claim 4 wherein the light pulses have a bandwidth of at least 900 nanometers.

6. The multidimensional spectrometer of claim 1 wherein a spectral range of the light pulses includes a wavelength of 1000 nanometers.

7. The multidimensional spectrometer of claim 6 wherein a spectral range of the light pulses includes a range of at least 400 to 1400 nanometers.

8. The multidimensional spectrometer of claim 1 wherein a spectral bandwidth, of the light pulses is no less than one and one half octaves.

9. The multidimensional spectrometer of claim 1 wherein the probe and PUMP pulses have a spectrum substantially identical to the source light pulses.

10. The multidimensional spectrometer of claim 1 wherein the at least one white light source is selected from the group consisting of a laser passing through a beam splitter to be received by separate static spectral broadening elements creating two source light pulses and a laser received by a single static spectral broadening element to create a single source light pulse passing through a beam splitter to create two source light pulses.

11. The multidimensional spectrometer of claim 10 wherein the static spectral broadening element is a YAG crystal.

12. The multidimensional spectrometer of claim 1 wherein the second optical path pros ides a bifringent crystal separating the light pulse into first and second differently polarized light pulses, the bifringent crystal followed by a polarization selective wedge delaying one of the first and second differently polarized light pulses and not the other; followed by a polarizer realigning the polarization of the first and second differently polarized light sources after delay of the one of the first and second differently polarized light pulses; wherein the polarization selective wedge is controlled by the electronic computer.

13. The multidimensional spectrometer of claim 12 wherein at least one of the first and second optical paths includes a controllable pulse delay element for changing a relative delay of the pump pulses with respect to probe pulses provided by the first optical system.

14. A method of spectrally analyzing material using a multi-dimensional spectrometer having:
 a sample volume holding a sample to be analyzed;
 a light detector proximate to the sample volume;
 at least one white light source providing source light pulses having a substantially continuous bandwidth of at least 500 nanometers;
 a first optical system directing the source light pulses through the sample volume as a series of probe pulses to be received by the light detector;
 a second optical system receiving the source light pulses to break the light pulses into at least first and second pump pulses having a controllable time separation between the first and second pump pulses and directing the at least first and second pump pulses through the sample volume; and
 an electronic computer system communicating with the light detector to receive electrical data therefrom and the second optical system controlling the time separation between the at least first and second pump pulses over multiple light pulses to generate a multidimensional spectrograph; the method comprising the steps of:
 (a) stimulating a sample in the sample volume with first and second pump pulses having a first time separation;
 (b) exposing the sample in the sample volume after step (a) with the probe pulse and measuring the light received at the detector;
 (c) repeating steps (a) and (b) over a range of time separations; and
 (d) processing in the electronic computer measurements at steps (b) to produce a two-dimensional spectrum.

15. The method of claim 14 wherein the light pulses have a bandwidth of at least 700 nanometers.

16. The method of claim 15 wherein the light pulses have a bandwidth of at least 1000 nanometers.

17. The method of claim 14 wherein a spectral range of the light pulses includes a wavelength of 1000 nanometers.

18. The method of claim 17 wherein a spectral range of the light pulses includes a range of at least 400 to 1400 nanometers.

19. The method of claim 14 wherein a spectral bandwidth of the light pulses is no less than one and one half octaves.

20. The method of claim 14 wherein the probe and PUMP pulses have a spectrum substantially identical to the source light pulses.

* * * * *